(12) United States Patent
Silver

(10) Patent No.: US 11,737,924 B2
(45) Date of Patent: Aug. 29, 2023

(54) FORWARD OSMOSIS MEDICAL AND WOUND CARE DEVICES

(71) Applicant: Brian H. Silver, Albany, OR (US)

(72) Inventor: Brian H. Silver, Albany, OR (US)

( * ) Notice: Subject to any disclaimer, the term of this patent is extended or adjusted under 35 U.S.C. 154(b) by 0 days.

(21) Appl. No.: 16/991,669

(22) Filed: Aug. 12, 2020

(65) Prior Publication Data
US 2020/0368410 A1 Nov. 26, 2020

Related U.S. Application Data

(63) Continuation-in-part of application No. PCT/US2020/017558, filed on Feb. 10, 2020.
(Continued)

(51) Int. Cl.
*A61F 13/00* (2006.01)
*A61M 1/00* (2006.01)
(Continued)

(52) U.S. Cl.
CPC .. *A61F 13/00063* (2013.01); *A61F 13/00068* (2013.01); *A61F 13/0206* (2013.01);
(Continued)

(58) Field of Classification Search
CPC ............ A61M 1/90; A61M 2205/7518; A61M 2205/7536; A61M 1/69; A61M 2205/75;
(Continued)

(56) References Cited

U.S. PATENT DOCUMENTS 4,671,267 A 6/1987 Stout
8,439,894 B1 * 5/2013 Miller .................. A61M 1/962
604/543
(Continued)

FOREIGN PATENT DOCUMENTS

WO WO-2020159859 A1 * 8/2020 ....... A61F 13/00029

OTHER PUBLICATIONS

"Glycerol (1,2,3-propanetriol) is a naturally occurring osmotic agent that reduces cerebral edema and improves brain perfursion", Hunter's Tropical Medicine and Emerging Infectious Disease (Ninth Edition) 2013 (Year: 2013).*
(Continued)

*Primary Examiner* — Erich G Herbermann
*Assistant Examiner* — Alessandro R Del Priore
(74) *Attorney, Agent, or Firm* — Dorsey & Whitney LLP

(57) ABSTRACT

Devices and methods herein remove water from human or animal biological waste fluids using one or more forward osmosis filters. The devices allow for the volume of liquid or semi-liquid waste, including potentially infectious liquid waste, to be filtered to reduce potential exposure of healthcare staff to infectious liquid waste. On a hospital, healthcare staff, or individual patient basis, removing water and concentrating the waste can reduce challenges in management and disposal of the waste. Devices herein use forward osmosis to manage and filter, using one or more suitably sized filter(s), biological fluid exudate from wounds. The devices can be constructed to transport water present in the exudate away from a wound. The wound treatment devices herein not only allow for fluid from wounds to be filtered but also provide structures that can protect wounds from external contaminants, including bacteria and viruses. The wound treatment devices can be incorporated into negative pressure wound therapy systems, if desired.

19 Claims, 9 Drawing Sheets

Related U.S. Application Data

(60) Provisional application No. 62/805,470, filed on Feb. 14, 2019, provisional application No. 62/804,759, filed on Feb. 13, 2019.

(51) Int. Cl.
  *B01D 61/00* (2006.01)
  *A61F 13/02* (2006.01)

(52) U.S. Cl.
  CPC ...... *A61F 13/0213* (2013.01); *A61F 13/0216* (2013.01); *A61F 13/0223* (2013.01); *A61M 1/98* (2021.05); *A61M 1/982* (2021.05); *B01D 61/002* (2013.01); *A61F 2013/00876* (2013.01); *A61M 1/60* (2021.05); *A61M 2205/7518* (2013.01); *A61M 2205/7536* (2013.01)

(58) Field of Classification Search
  CPC ...... A61M 1/0001; A61M 1/98; A61M 1/982; A61M 1/60; A61M 1/915; A61F 13/0206; A61F 13/0213; A61F 13/0216; A61F 13/0223; A61F 2013/00876; A61F 13/00063; A61F 13/00068; B01D 61/002; B01D 63/087
  See application file for complete search history.

(56) References Cited

U.S. PATENT DOCUMENTS

| | | | |
|---|---|---|---|
| 2008/0215020 A1* | 9/2008 | Reeves | A61M 1/916 604/305 |
| 2011/0203994 A1 | 8/2011 | McGinnis et al. | |
| 2012/0316538 A1* | 12/2012 | Heiser | A61M 1/60 604/543 |
| 2014/0243762 A1* | 8/2014 | Aali | A61F 13/0223 604/290 |
| 2014/0276497 A1* | 9/2014 | Robinson | A61M 1/882 604/319 |
| 2020/0368410 A1 | 11/2020 | Silver | |
| 2022/0079815 A1* | 3/2022 | Edwards | A61F 13/0276 |

OTHER PUBLICATIONS

"Glycerol (1,2,3-propanetriol) is a naturally occurring osmotic agent that reduces cerebral edema and improves brain perfursion", Hunter's Tropical Medicine and Emerging Infectious Disease (Ninth Edition) 2013 (Year: 2013) (Year: 2013).*
U.S. Appl. No. 62/804,759, filed Feb. 13, 2019.
U.S. Appl. No. 62/805,470, filed Feb. 14, 2019.
International Search Report and Written Opinion from International Application No. PCT/US2020/017558 dated Apr. 27, 2020.
International Search Report and Written Opinion from International Application No. PCT/US2021/045551 dated Nov. 17, 2021.
U.S. Appl. No. 17/430,169, filed Aug. 11, 2021.
Stout, et al., "Glycerin-Based Hydrogel for Infection Control", Advances in Wound Care, Jan. 9, 2012, pp. 48-51.

* cited by examiner

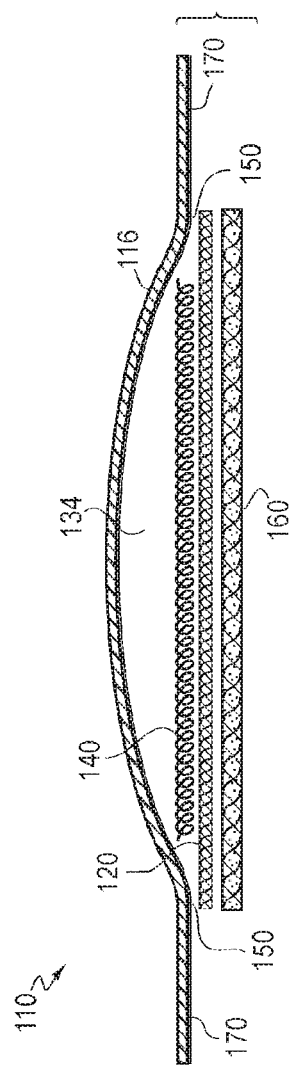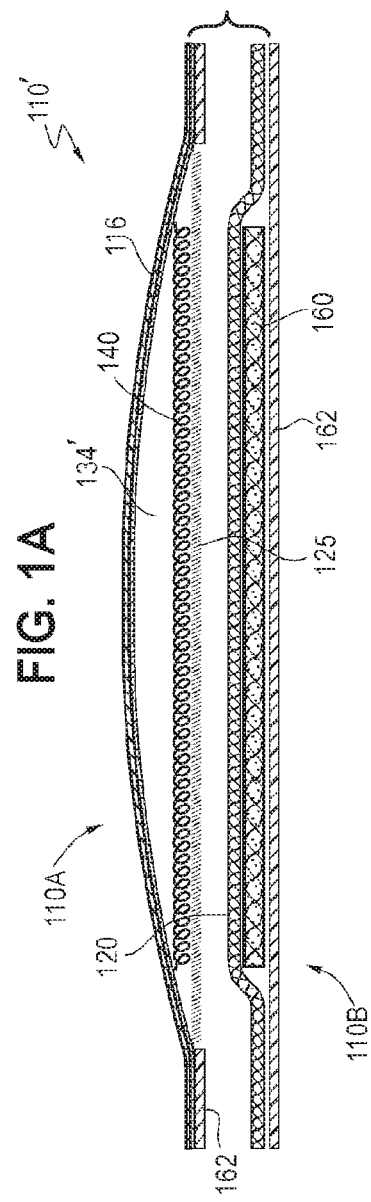

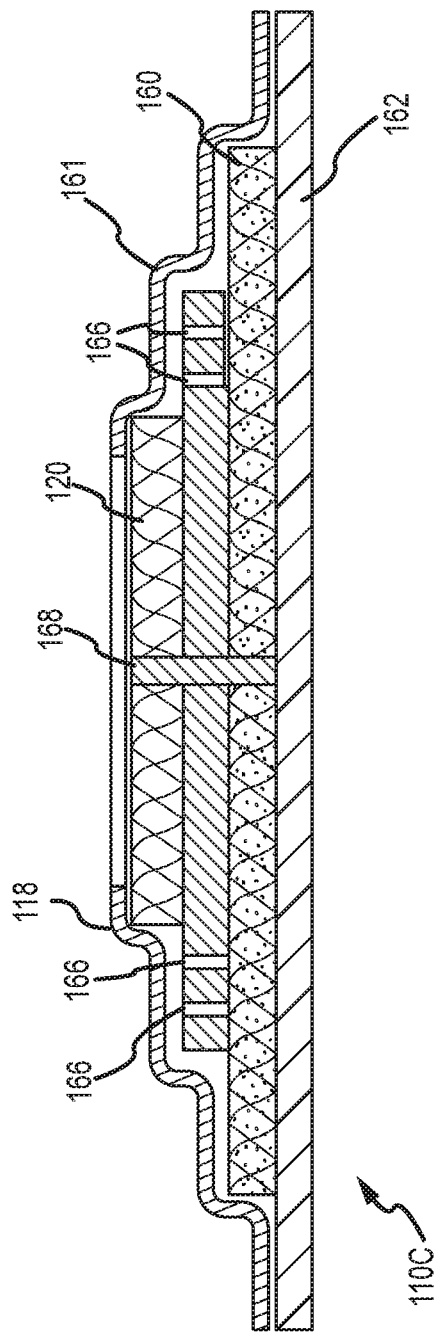

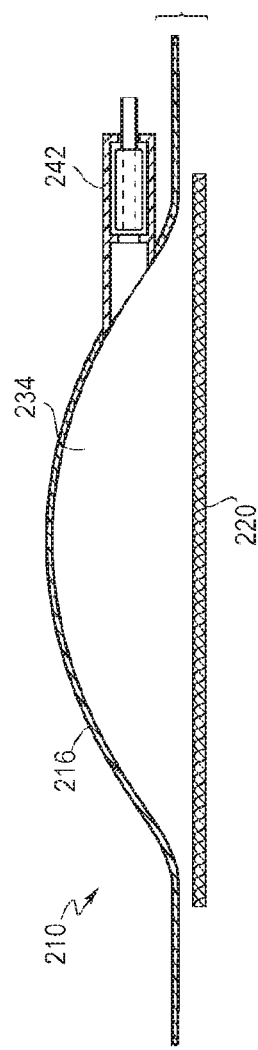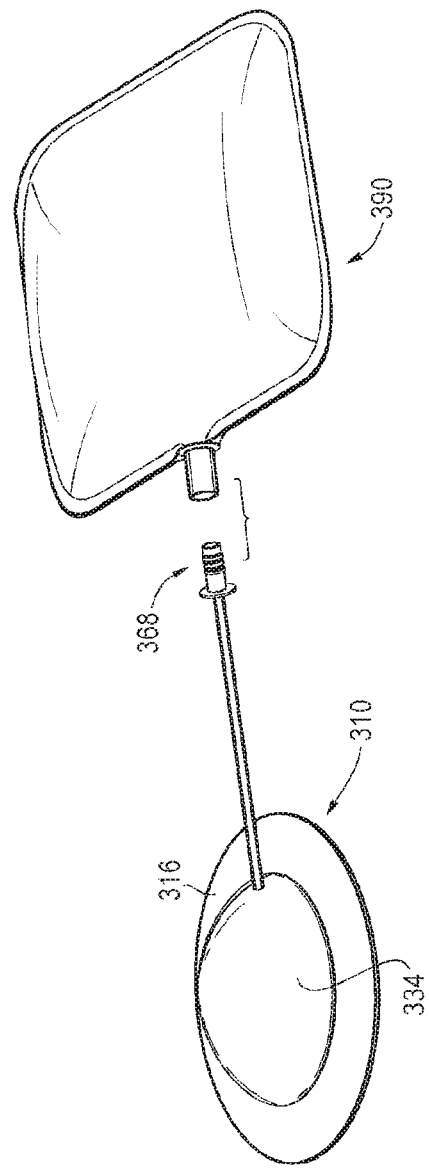

FORWARD OSMOSIS MEDICAL AND WOUND CARE DEVICES

CROSS-REFERENCE TO RELATED APPLICATIONS

This application is a continuation-in-part of International Application No. PCT/US20/17558 filed on Feb. 10, 2020, which application relates to and claims priority from U.S. Application No. 62/804,759, for "BIOLOGICAL FLUID WATER REMOVAL DEVICE AND METHOD" filed 13 Feb. 2019 and U.S. Application No. 62/805,470, for "FORWARD OSMOSIS WOUND CARE DEVICE" filed 14 Feb. 2019, the contents of each of which are incorporated herein by reference in the entirety.

BACKGROUND OF THE DISCLOSURE

Many types of wound care dressings are used to promote healing of the wound and to protect the wound from further harm or contamination. Dressings are available in many materials, constructions, sizes, and shapes. Dressings vary depending on the type and severity and size of the wound, the anatomical location of the wound, the amount of blood and other exudate that needs to be managed, skin conditions, and treatment approach. Wound dressing types can include hydrocolloid, hydrogel, alginate, collagen, foam, transparent, gauze, and non-woven, for example. Additionally, there are various agents, such as antimicrobials or pain relief pharmaceuticals, that may be incorporated into the dressing, if needed or desired.

In combination with specific wound care dressings, negative pressure wound therapy (NPWT) can be used to treat hard to heal wounds and has been shown to increase blood flow, reduce edema, enhance wound contraction, and stimulate the formation of granulation tissue. NPWT can be used for various types of wounds such as surgical wounds, open abdominal incisions, dehisced wounds, partial thickness burns, diabetic ulcers, pressure ulcers, flaps and grafts, and traumatic wounds. Traditional NPWT has wound dressings that are used in combination with a canister for collecting wound exudate as part of the NPWT system. There is at least one disposable NPWT system that is canister-less and keeps the wound exudate within the wound dressing while a portion of the water in the exudate exits the dressing as water vapor through a water vapor permeable polyurethane film portion of the dressing. This type of disposable NPWT system is smaller, provides for enhanced patient mobility, and is lower cost than traditional NPWT pump systems.

NPWT dressings are typically changed every 2-3 or 3-4 days, depending on the level of exudate, contamination considerations, condition of the dressing, etc. which may result in more frequent changes. Some manufacturers indicate that use may be extended up to 7 days at the clinician's discretion.

Exudate is accumulated fluid in a wound. There are various types of wound exudate including: serous exudate, which is clear, thin, watery plasma; sanguineous exudate, which is fresh bleeding that is seen in deep partial-thickness and full-thickness wounds; serosanguineous exudate, which is thin and watery with red blood cells providing a pink tinge; seropurulent exudate, which is thin, watery, cloudy, and appears yellow to tan; and purulent exudate, which is thick and opaque and appears tan, yellow, green, or brown.

Management of blood and other exudate from the wound is important for wound healing. Excess wetness can damage surrounding tissue, lead to wound infection, be uncomfortable for the patient, and create a strong odor. Ideally the wound is kept moist but not overly moist. Inventive wound dressings can provide alternative approaches beneficial to managing wound exudate and be beneficial to wound healing.

There are many biological waste fluids that are disposed of in hospitals, clinics, long term care centers, laboratories, and other healthcare facilities, as well as home health care settings. These fluids are often disposed of in biohazard bags or into the sanitary sewer. Bagged fluid waste needs to be controlled and can be expensive to manage. Having healthcare staff empty biological waste fluids into the sanitary sewer creates the potential for staff exposure to potentially infectious fluids. While there are washing systems available that empty directly to the sanitary sewer system, such as Skyline Medical's Streamway System, they are not available in many settings and are not used to process many of the body fluids that need disposal.

Reduction in the volume of potentially infectious fluids is also useful when there is not a safe location for storage or disposal of the waste, for example where there is no sanitary sewer system immediately available or capability to manage large volumes of bagged liquid waste. Personal care medical devices used for collection of liquid or semi-liquid biological waste also have handling challenges for management and disposal of the waste. Removal of water from these fluids via forward osmosis, on a hospital or healthcare staff or individual patient basis, concentrates the waste and can reduce challenges in management and disposal of the waste.

SUMMARY

Forward osmosis wound care devices are set forth. The forward osmosis wound care devices can be of general construction or customized to the specific wound care application and setting. The forward osmosis device is designed to allow water in the fluid exiting the wound to be pulled away from the wound. Fluid transported through the forward osmosis filter to the non-wound side of the forward osmosis layer of the dressing is predominantly water as bacteria, viruses, and most other components do not pass through the filter. The water can then be taken up by an absorbent layer, stored within a liquid storage compartment of the device, or transferred out of the system such as via suction or gravity drainage or evaporation or removal and replacement of the absorbent layer or removal and replacement of the storage compartment or any combination of the above. Filtrate can also be forced out of the wound care device via the positive pressure created as a volume of liquid is osmotically pulled across the forward osmosis filter. While water is removed from the wound exudate, the wound is kept moist.

The forward osmosis wound care dressings disclosed herein have significant advantages compared to conventional wound care dressings. Many embodiments of the osmotic wound dressings described herein use a forward osmosis membrane that passively separates water out of the exudate and draws that water away from the wound to an area that is separate and isolated from the wound, on the non-wound side of the forward osmosis filter which is also a bacterial and viral barrier. Advantageously, this reduces the volume of liquid exudate material available for bacterial colonization near the wound area. Additional advantages of moving this volume of liquid to the non-wound side of the filter membrane, especially when combined with transferring the filtrate out of the system such as via suction or gravity drainage or evaporation or removal and replacement of the absorbent layer or removal and replacement of the storage compartment or any combination thereof, include that it can increase the time between dressing changes, decrease the number of dressing changes and associated disturbance of the wound, and improve the ability to handle higher flow rates and volumes of exudate. This can result in reduced cost, improved patient comfort, improved patient care, less disruption of the wound healing process, and less contaminated wound dressing waste that needs to be handled by the hospital staff or other caregiver or patient.

For disposable NPWT systems where the wound dressing collects all the exudate instead of collecting the exudate in a canister, incorporating a forward osmosis system to pull out the water, with or without inclusion of the high moisture vapor transmission film currently used to allow water to exit the NPWT dressing, may allow for handling of certain wounds where currently traditional NPWT is recommended as the system of choice in order to handle higher exudate rates. This can be a significant advantage as disposable NPWT is less costly, less bulky, and more portable than traditional NPWT systems.

As water is pulled from the wound exudate and through the forward osmosis filter, it potentially creates some of the wound healing benefits seen with negative pressure wound therapy. In some cases, flushing the wound with water or saline, preferably sterile, may be beneficial in priming the forward osmosis system. If the forward osmosis dressing and traditional NPWT are used together, there may even be further benefits than with either used alone including but not limited to less frequent dressing changes, less frequent canister changes, less potentially infectious waste, and less blockage of the vacuum path, for example.

The forward osmosis filter can be used in conjunction with another filtering material that keeps various blood components as well as other components in the exudate from potentially clogging or otherwise reducing the efficiency of fluid transfer across the forward osmosis membrane.

Draw materials or draw solutes or osmotic agents, such as salts, sugars including sugar alcohols such as glycerin, or both, are used to draw water from the blood or other exudate and across the filter, leaving potentially infectious agents and other materials behind. In some embodiments, the system does not need application of electrical energy or electrochemical energy to transport water across the forward osmosis membrane. This transfer of fluid across the forward osmosis filter reduces the volume of potentially infectious fluids for management and disposal. The solute or solutes or draw material or draw materials can be provided in a multitude of forms including but not limited to crystals, sheets, pills, brine, or impregnated into or onto other substrates such as foam or gauze or gel or other materials or the like. The selected substrate allows the draw material to effectively function in getting water to cross the forward osmosis membrane.

Glycerin can be used as a draw material and it can be otherwise incorporated into the wound dressing to enhance treatment of the wound. U.S. Pat. No. 4,671,267 describes a moisture sorbing gel including a humectant such as glycerin. Glycerin contained in a gel, in suppository sections, on wicking material, on gauze, and on other materials effectively draws water across the forward osmosis membrane of a wound care dressing. Glycerin is advantageous as the draw material for the wound dressing in that it also absorbs water with high affinity.

The forward osmosis device may also contain chemicals or other materials on the filter material or separate from the filter material and on either side or both sides of the filter material to reduce odor, reduce bacterial or viral load, block or bind or transform specific components present in the biological fluid, or absorb left over liquid, for example. Such materials can include but are not limited to activated charcoal, antimicrobials, foam, gauze, sodium polyacrylate, secondary filters, or paper fluff or the like.

The forward osmosis filter material can have different constructions. For example, the forward osmosis filter can be configured of one or more suitable semi-permeable forward osmosis membranes having preselected pore size based on the construction and intended use of the product. Constructions resulting in an overall, small pore size can be used for a wound care dressing, for example. Standard high flux forward osmosis cellulose triacetate membranes produced by Forward Technology Solutions (FTS) of Albany, Oreg. that are currently used for freshwater hydration products have properties that function well for the forward osmosis wound dressing inventions presented herein as they have good rejection of most dissolved particles, a good flow rate capability, with minimal reverse flow to the wound side of the membrane. This membrane or filter, which includes a backing material incorporated as part of the membrane, contains glycerin as manufactured which helps to initiate the forward osmosis process even without another draw material source. The backing material side of the membrane contains the majority of the glycerin and is therefore preferably positioned on the filtrate or permeate side of the membrane while the non-backing material side of the filter is preferably on the retentate side of the membrane for the wound dressing. In some wound dressing applications, for example a wound with an initially high level of exudate that quickly reduces to a relatively low level of exudate, the glycerin that is included as part of the membrane as manufactured may be the only source of draw material needed. An additional amount of glycerin may be incorporated into the filter compared to current standard production amounts of glycerin.

In some applications, movement of the liquid via shaking, vibration, or cross flow along the membrane surface of either or both the draw solution and the exudate may be used to improve performance. The exudate may be combined with sterile water or saline to increase volume and/or decrease viscosity.

The device may also contain manual measurement markers or electronic sensor approaches for monitoring parameters such as total or current fluid output, time markers, concentration of draw solution, pressure, exudate handling capacity available, and other pertinent information. This information as well as associated warning conditions can be recorded by or made available to the healthcare provider, other caregiver, or patient. Collected data can be electronically stored, analyzed, and transmitted.

The wound dressing is secured in place. Depending on the wound type, location, size, and other factors, different approaches to secure the dressing can be used including, but not limited to, adhesive applied on at least one of the dressing layers that has direct access to the skin around the periphery of the wound, using a roller bandage, using a tacky silicone layer, taping the edges, and applying an adhesive bandage over the dressing or the like.

The device may also include various positioning, holding and handling features that simplify placement and use.

In addition to forward osmosis wound care devices, general forward osmosis devices and forward osmosis methods of use for processing biological waste fluids are set forth. The forward osmosis devices can be of general construction or customized to the specific application and biological waste fluid that is being handled. The forward osmosis device is designed to allow the fluid to be readily input into the device, minimizing exposure by the healthcare worker, the patient, or other individual processing the fluid. In at least one embodiment, forward osmosis filter material is incorporated into the biologic waste fluid collection system.

In at least one other embodiment, the forward osmosis membrane is in a device that is not directly incorporated into the biologic waste fluid collection device. Any transfer of the body waste fluid from the patient to the forward osmosis device or from one or more fluid collection or storage devices to the forward osmosis device is designed to minimize potential exposure to the biological waste fluid. The forward osmosis device may also include an outlet to allow the processed fluid to be emptied from the device.

Gravity, peristaltic pumps, suction pumps, and other approaches can be used to transfer the biologic waste fluid into the forward osmosis device as well as transfer the filtrate or permeate out of the forward osmosis device.

Draw materials or draw solutes or osmotic agents, typically salts or sugars or both, are used to draw water from the biological waste fluid and across the filter, leaving potentially infectious agents and other materials behind. This transfer of fluid across the forward osmosis filter reduces the volume of liquid or semi-liquid waste, including potentially infectious fluids, for disposal. The solute or solutes or draw material or draw materials can be provided in a multitude of forms including but not limited to crystals, sheets, pills, brine, or the like, or impregnated into or onto other substrates such as foam or gauze or gel or other materials. The selected substrate allows the draw material to effectively function in getting water to cross the forward osmosis membrane.

The forward osmosis device may also contain chemicals or other materials on the filter material or separate from the filter material and on either side or both sides of the filter material to reduce odor, reduce bacterial or viral load, block or bind or transform specific components present in the biological waste fluid, or absorb left over liquid, for example. Such materials can include but are not limited to activated charcoal, antimicrobials, foam, gauze, sodium polyacrylate, secondary filters, or paper fluff or the like.

The device may also contain manual measurement markers or electronic sensor approaches for monitoring parameters such as total or current fluid input, total or current fluid output, fluid transferred, time markers, concentration of draw solution, and other pertinent information. This information as well as associated warning conditions can be recorded by or made available to the healthcare provider. For an automated or semi-automated system, measurements can trigger activation of input and output valves or pumps or other devices used to manage the retentate, filtrate, or draw material.

The device may also include various holding and handling features that simplify positioning and maneuvering.

Forward osmosis devices for removing water from biological waste fluids can be part of personal care medical devices used for collection of liquid or semi-liquid biological waste, including but not limited to urological and ostomy devices such as urine leg bags, urostomy bags, ileostomy pouches, etc.

Methods for using the device are for providing for an input of fluid into the system, providing a forward osmosis filter and solute(s) to transfer water from the biological waste fluid side of the filter, and providing for an outlet for removal of the water from the device on the non-biological waste fluid side of the filter.

In some exemplary embodiments, a wound treatment device in accordance with the principles herein can include a forward osmosis filter and a cover layer. The filter is incorporated into a wound dressing and configured to be placed over a wound area and secured to a patient. The filter includes a semi-permeable forward osmosis filter or a forward osmosis membrane configured to remove liquid water from wound drainage fluid (including wound exudate) by allowing the liquid water to pass through the filter and inhibiting other components in the wound drainage fluid from passing through the filter such that the liquid water is substantially free of the other components. The semi-permeable forward osmosis filter or the forward osmosis membrane of the filter also are configured to prevent or inhibit substantially all of one or more of draw materials, liquids, and bacterial contaminants from passing through the filter in the reverse direction toward the wound area. The filter includes glycerin as an osmotic agent or a draw material effective to provide at least some of the osmotic potential to passively transport at least a portion of the liquid water from the wound drainage fluid through the filter without application of electrical energy or electrochemical energy. The cover layer is directly or indirectly connected to the filter to form a protective barrier over the wound and prevent ingress of liquids, bacteria, and viruses to the wound area. The cover layer includes at least a portion of semi-permeable high moisture vapor transmission rate material that is fluidly connected with the at least one of the would drainage fluid or the wound exudate in the wound area such that at least some of the water from the would drainage fluid passes through the high moisture vapor transmission rate material as water vapor, thereby aiding in overall water removal from the wound area to complement the liquid water removed through the filter.

In an exemplary embodiment, the wound treatment device includes one or more absorbent materials positioned on a non-wound side of the filter and in fluid communication with the filter to absorb at least a portion of the liquid water mixed with the draw material. In some embodiments, at least one of the one or more absorbent materials may be removable and replaceable.

In an exemplary embodiment, the wound treatment device includes a supportive backing material positioned on a non-wound, non-patient side of the filter. The supportive backing material contains more glycerin than the glycerin on a wound side of the filter.

In an exemplary embodiment, the wound treatment device includes at least one of a high moisture vapor transmission rate material or a material having areas open to the surrounding air positioned on a non-wound side of the filter. At least one of the high moisture vapor transmission rate material or the material having areas open to the surrounding air facilitate evaporation of at least some of the liquid water off the filter after the liquid water has been moved to the non-wound side of the filter.

In an exemplary embodiment, the wound treatment device includes one or more other locations of an additional osmotic agent or an additional draw material positioned on a non-wound side of the filter to be in contact with the filter for at least some portion of a time the wound dressing is applied to the patient. The additional osmotic agent or the additional draw material may be added to the wound treatment device during set-up or during use.

In an exemplary embodiment, the wound treatment device includes at least one chamber or compartment, the at least one chamber or compartment configured to collect liquid or permeate processed by the wound treatment device and securable to the forward osmosis membrane. In some embodiments, the wound treatment device also may include at least one of an absorbent layer or a wicking layer in the at least one chamber or compartment. The absorbent layer or wicking layer may be removable or replaceable from the at least one chamber or compartment. The at least one chamber or compartment may be removable and replaceable from the filter. The filter or an area around the filter may be secured to a second layer of material to form the at least one chamber or compartment. The second layer of material may be configured to provide a high rate of water vapor transmission. The wound treatment device also may include a port providing access to the at least one chamber or compartment, the port being sized and dimensioned for addition or removal of materials from the at least one chamber or compartment.

In an exemplary embodiment, the wound treatment device is part of a negative pressure wound therapy system.

In an exemplary embodiment, the wound treatment device includes a wicking layer positioned on the wound treatment device to be between the wound and the filter. The wicking layer is configured to distribute liquid from the wound exudate over a larger area of both sides of the wicking layer and thus to a larger area of the filter thereby enhancing the transfer of the liquid water to a non-wound side of the filter.

In accordance with the principles herein, a system for treating and healing wounds can include a forward osmosis wound dressing device and a port. The forward osmosis wound dressing device has a forward osmosis filter and a confined space on a non-wound side of the filter. The wound dressing is configured to cover a wound and transport at least some portion of a water component of a wound fluid exudate away from the wound through the forward osmosis filter and then into the confined space on the non-wound side of the filter. The confined space limits an amount of filtrate mixed with draw material contained in the confined space. The port is fluidly connected to the confined space. When the confined space is full or nearly full of liquid, water coming through the filter forces the filtrate mixed with the draw material out of the confined space via the port and out of the wound dressing device. The wound dressing device is configured to be connectable to a secondary collection compartment that collects the filtrate transported out of the wound dressing device. At least a portion of the secondary collection compartment material may be for a high rate of water vapor transmission.

The device can be configured wherein at least a portion of the area on the wound side of the forward osmosis filter where wound exudate can be present is fluidly connected to a material that both prevents bacterial ingress and has an increased or high moisture vapor transmission rate as is commonly used in some advanced wound care products, for example polyurethane film from 3M or from Smith & Nephew, thereby providing more than one path for water from the wound exudate to move out of that area. Water vapor can go through the high moisture vapor transmission rate material and liquid water can go through the forward osmosis membrane. Both the forward osmosis filter and the high moisture transmission rate film are semi-permeable materials. For NPWT systems, the vacuum source and associated connection to the patient side of the forward osmosis membrane of the wound care dressing provides yet another path for water to move out of that area.

The device can be configured wherein at least a portion of the secondary collection compartment material provides for water vapor transmission at an increased or a high rate compared to devices without the secondary collection compartment material.

A negative pressure wound therapy dressing can be constructed in accordance with the principles herein. In an embodiment, a system for negative pressure wound therapy dressing for a wound area includes a vacuum access port and a forward osmosis membrane or filter. The vacuum access port is configured for application of a vacuum to the wound area. The forward osmosis membrane or filter is configured to remove water from at least some portion of wound exudate of the wound area. The forward osmosis membrane or filter includes a draw material, a supportive backing, one or more other locations of additional draw material, and a cover layer. The draw material includes glycerin and is configured to passively transport at least a portion of liquid water from wound drainage fluid of the wound area through the forward osmosis membrane or filter. The supportive backing material is positioned on a non-wound side of the dressing. The backing material contains more glycerin than the glycerin on a wound side of the forward osmosis filter. One or more other locations of draw material are on the non-wound side of the forward osmosis membrane or filter. The draw material from at least one of the one or more other locations is positioned to be in contact with the forward osmosis membrane or filter for at least some portion of time the dressing is applied to the patient. The cover layer is directly or indirectly connected to the forward osmosis membrane or filter to form a protective barrier over the wound area effective to prevent ingress of liquids, bacteria, and viruses to the wound area. The cover layer includes at least a portion of semi-permeable high moisture vapor transmission rate material that is configured to be fluidly connected with the wound exudate in the wound area to allow at least some of the water from the wound exudate to pass through the high moisture vapor transmission rate material as water vapor, thereby aiding in overall water removal from the wound area to complement the water removed through the forward osmosis filter.

In an exemplary embodiment, some portion of the water exudate is removed and transported away from the dressing via the vacuum for collection into a container.

In an exemplary embodiment, the system also includes a second collection compartment for managing wound exudate fluid. The secondary collection compartment is configured to have a connection point connectable to a wound dressing, separated from the wound dressing, configured to store liquid entering the secondary collection compartment via the connection point, and located near the patient. At least a portion of the secondary collection compartment material may provide for a high rate of water vapor transmission. For example, the secondary collection compartment material provide a water vapor transmission rate of at least about 1000 g/m$^2$/24 hours, at least about 1375 g/m$^2$/24 hours, at least about 3000 g/m$^2$/24 hours, or between about 1000 g/m$^2$/24 hours and about 3000 g/m$^2$/24 hours.

Additionally, the wound dressing can incorporate a semi-permeable material that is fluidly connected to the area on the wound side of the one or more forward osmosis membranes. The semi-permeable membrane prevents liquids and prevents bacteria from passing through the material toward the wound area and has an increased or high moisture vapor transmission rate going out of the wound area. The semi-permeable material may also allow oxygen to pass through it into the wound area. Such a semi-permeable material can be, for example, polyurethane film as is commonly used in negative pressure wound therapy products such as the Pico system from Smith & Nephew.

The device can be configured wherein some portion of the exudate is removed and transported away from the dressing via the vacuum for collection into a container.

The device can be configured wherein some portion of the water in the filtrate is removed from the wound dressing via transfer as water vapor through a material with a high moisture vapor transmission rate.

A wound dressing can be constructed in accordance with the principles herein. In an embodiment, the wound dressing includes a forward osmosis filter and one or more absorbent materials. The forward osmosis filter has a wound side of the filter and a non-wound side of the filter. The filter contains glycerin on at least the non-wound side of the filter, provides a protective barrier for a wound whereby bacteria and viruses do not pass through the filter from the non-wound side of the filter, and includes an area on the wound side of the forward osmosis filter for containing wound exudate having a water component. The one or more absorbent materials contain glycerin and are directly or indirectly mating with the non-wound side of the filter. The filter is capable of retaining non-water components from the wound exudate on the wound side of the filter. The absorbent material is capable of absorbing at least a portion of said water component from the wound exudate that passes through the filter from the wound side to the non-wound side of the filter. The absorbent material containing glycerin may be a gel containing glycerin.

A device for managing wound exudate fluid is set forth. The device can include a secondary collection compartment configured to have a connection point connectable to a wound dressing. The secondary collection compartment can be separated from the wound dressing, if desired. The secondary collection compartment can be configured to store liquid entering the secondary collection compartment via the connection point. The secondary collection compartment can be configured to facilitate a position located near the patient.

The device can be configured wherein at least a portion of the secondary collection compartment material provides for a high rate of water vapor transmission.

An exemplary device for treating biological waste fluids in accordance with the principles herein can include a first chamber for inputting at least one biological waste fluid; a filter functioning as a forward osmosis filter to remove water from the biological waste fluid, the filter configured to be connectable to said first chamber; the forward osmosis filter connectable between the first chamber and a second chamber, the second chamber for collecting the processed liquid or filtrate; at least one draw material to provide the osmotic drive to transfer or pull water from the first chamber into the second chamber; the draw material located in the second chamber and the draw material in contact with the filter.

An exemplary system for treating biological waste fluids can include: at least one chamber for receiving one or more biological waste fluids; a filter in contact with a first chamber; draw material connectable to the filter; the filter functioning as a forward osmosis filter to remove water from the biological waste fluid while keeping bacterial and viral contaminants from passing through the filter.

Another exemplary system for treating biological waste fluids can include a forward osmosis filter to convert the waste fluid to reduce the volume of potentially infectious liquid waste and reduce healthcare staff exposure to potentially infectious liquid waste.

The exemplary system can include chemicals or other materials on the filter material or separate from the filter material and on either side or both sides of the filter material to reduce odor, reduce bacterial or viral load, block or bind or transform specific components present in the biological waste fluid, or absorb left over liquid or the like.

Embodiments of methods according to the principles herein can include providing for an opening into a first chamber for input of biological waste fluid into the first chamber; providing a forward osmosis filter in contact with the first chamber; separating the first chamber from a second chamber with the forward osmosis filter; positioning the forward osmosis filter for contact with at least a portion of the biological waste fluids input into the first chamber; and providing for an outlet for removal of filtrate from the second chamber.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF DRAWINGS

FIG. 1 is a partial cross-sectional drawing of a wound dressing with forward osmosis filter, according to an embodiment.

FIG. 1A is an alternate construction of FIG. 1 separating the wound dressing with forward osmosis filter into two sections, according to an embodiment.

FIG. 1B is a cross-sectional view of a wound dressing, according to an embodiment.

FIG. 2 is a partial cross-section drawing of an access port, according to an embodiment.

FIG. 3 is a perspective view of a wound dressing with forward osmosis filter and secondary collection compartment, according to an embodiment.

DETAILED DESCRIPTION

Figure 1C:
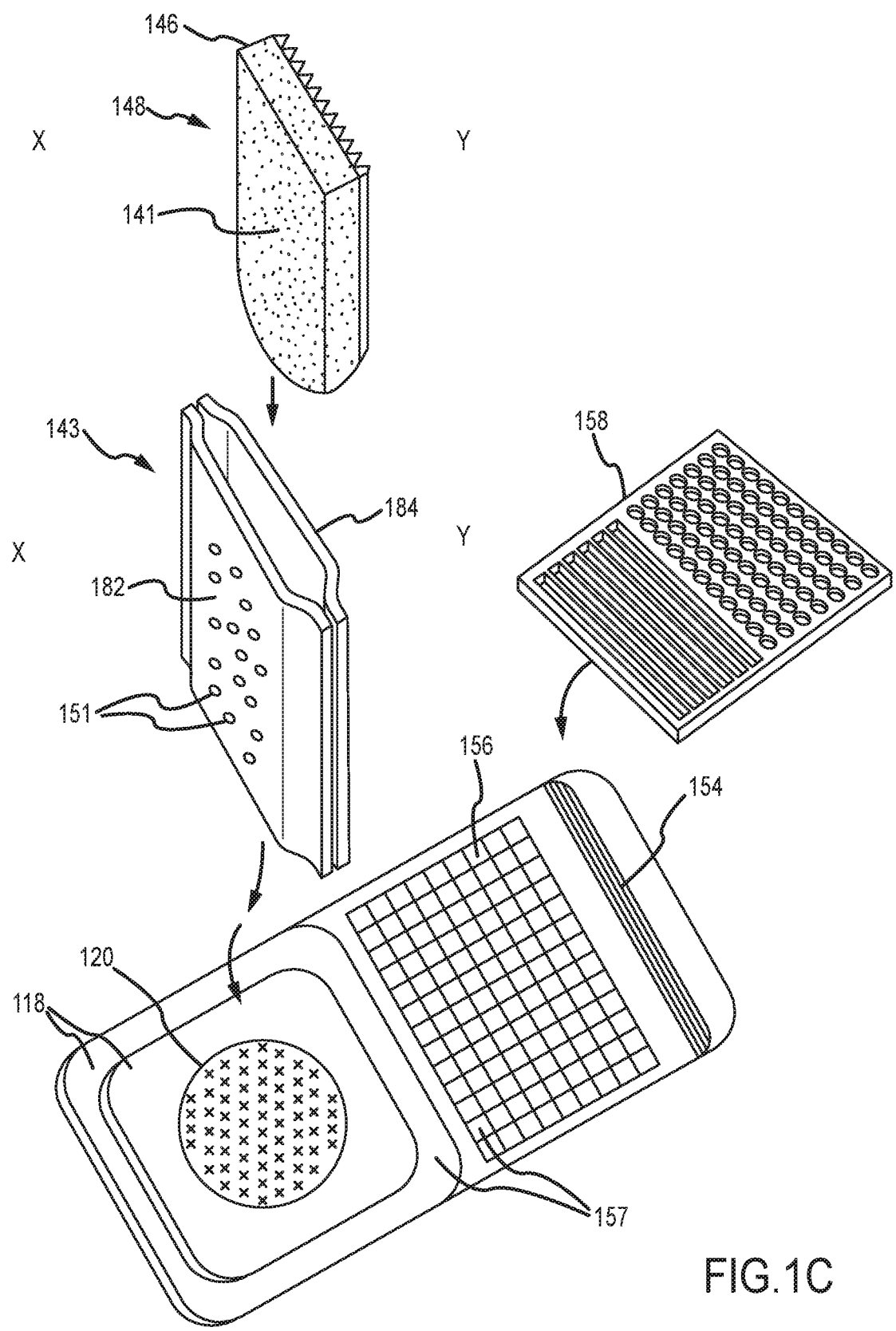
FIG. 1C is an exploded view of a wound dressing including a glycerin gel pad assembly, according to an embodiment.

Forward osmosis is used in a variety of applications including but not limited to: concentrating or dewatering foods and beverages; managing industrial wastewater, landfill leachate, and mineral concentration; power generation; controlled delivery of pharmaceuticals; and personal hydration. The fraction of feed material that passes through the membrane is permeate or filtrate while the fraction that is retained by the filter is retentate. Many embodiments of wound care devices and wound dressing systems described herein include a forward osmosis filter or membrane. FIG. 1, for example, shows a wound dressing 110 with a filter material 120 capable of allowing water to pass through the filter 120 via osmotic pressure while preventing most other components, including most of the bacteria and viruses, from passing through. In this embodiment, the wound dressing has at least a forward osmosis filter layer 120 and a second layer 116, which can be a sheet of material, secured to the filter layer 120 at the perimeter 150 to form at least one compartment or chamber 134 between the filter layer 120 and the second layer 116. The second layer 116 is made of a material that does not let liquid or solid materials that are in the chamber 134 to pass through it.

The chamber or chambers 134 include draw solute(s) or draw material(s) 140. Exudate from the wound contacts the forward osmosis filter 120 and a portion of the water in the fluid is transported or pulled through the filter into the chamber(s) 134 by forward osmosis leaving other materials from the exudate on the wound side of the filter including bacteria and viruses. Exudate can be considered biological waste fluid. Biological waste fluid as used herein can include, but is not limited to, wound exudate, blood, urine, digestive fluids, digestive output, sputum, cerebral spinal fluid, lymph and the like once removed from the body and no longer needed. In some embodiments, the filter 120 is configured to remove liquid water from wound drainage fluid by allowing the liquid water to pass through the filter and inhibiting the other components in the wound drainage fluid from passing through the filter such that the liquid water is predominantly or substantially free of the other components. Liquid water that is substantially free of other components may include liquid water in which the filter 120 has prevented or inhibits at least 99%, at least 95%, at least 90%, at least 85%, at least 80%, at least 75%, or at least 50% of the other components from passing through the filter 120 with the liquid water. In some embodiments, the filter 120 may initially inhibit or prevent at least one salt including one or more of salt, sodium, potassium, chloride or other ions from passing through the filter 120 to the non-wound side, but allow the at least one salt to pass through the filter 120 over time. For example, the filter 120 may allow a maximum of about 1% of the at least one salt to pass through the filter 120 per hour, a maximum of about 2.5% of the at least one salt to pass through the filter 120 per hour, a maximum of about 5% of the at least one salt to pass through the filter 120 per hour, a maximum of about 10% of the at least one salt to pass through the filter 120 per hour, a maximum of about 15% of the at least one salt to pass through the filter 120 per hour, a maximum of about 20% of the at least one salt to pass through the filter 120 per hour, a maximum of about 25% of the at least one salt to pass through the filter 120 per hour, a maximum of about 30% of the at least one salt to pass through the filter 120 per hour, a maximum of about 40% of the at least one salt to pass through the filter 120 per hour, or a maximum of about 50% of the at least one salt to pass through the filter 120 per hour. Passage of the one or more of salt, sodium, potassium, chloride or other ions from passing through the filter 120 to the non-wound side may be beneficial to wound healing because these salts are osmotic agents and when on the wound side of the filter can negatively impact the flow of water across the filter to the non-wound side. In some embodiments, the filter 120 allows the at least one salt to pass through the filter 120 when applied to the wound area.

The filter 120 also may prevent or inhibit substantially all draw materials, liquids, and bacterial contaminants from passing through the filter 120 in the reverse direction toward the wound area. Preventing or inhibiting substantially all draw materials, liquid, and bacterial contaminants from passing through the filter 120 in the reverse direction toward the wound area may include preventing or inhibiting at least at least 99%, at least 95%, at least 90%, at least 85%, at least 80%, at least 75%, or at least 50% of the draw materials, liquid, and bacterial contaminants from passing through the filter 120 in the reverse direction toward the wound area. The second layer 116 extends beyond the seal perimeter 150 and incorporates an adhesive 170 to provide a way for securing the wound dressing 110 to the patient and covering the wound.

The second layer 116 may be optionally made of a material that provides for moisture vapor transmission through it to reduce the amount of liquid contained in the chamber 134. The water vapor transmission rate (MVTR) is comparable with other commonly used wound care dressings, such as those made of single or multilayer thermoplastic polyurethanes. The MVTR for these materials can be adjusted for the specific application. Higher MVTR materials, including higher MVTR polyurethane, are preferred. For example, a polyurethane film with an active area of 10 cm×10 cm and a MVTR of 3000 $g/m^2/24$ hours, would allow a nominal 30 g of water vapor to pass through in 24 hours.

As water vapor leaves the wound dressing through this material, the draw material becomes more concentrated allowing for continued osmotic action. The draw material can pull additional water through the filter membrane which can then pass through the polyurethane film as water vapor and the cycle continues. Preferably, the moisture vapor transmission rate is great enough to keep the chamber 134 from completely filling with water and/or substantially diluting the draw material 140 such that it is no longer effective in pulling water across the membrane 120. At a lower MVTR, chamber 134 may fill up faster. The second layer 116 may be optionally made of stretchable material to allow it to expand and provide for a larger volume inside the chamber 134. This expansion can be measured manually or with electronic sensors to identify the amount of fluid inside the chamber. Alternatively, the second layer 116 can be a rigid or semi rigid material and can be a defined shape, such as a hollow hemisphere. An air vent may be included. As yet another alternative, to promote evaporation, the second layer 116 can have one or more openings in the material, including but not limited to open sides, in conjunction with an absorbent material in chamber 34 to reduce the potential for water or draw materials leaking out.

Other items can be added to the wound dressing 110 such as for reducing odor, reducing bacterial or viral load, blocking or binding or transforming specific components present in the biological fluid, adding or changing color, or absorbing liquid or the like.

Additional layers can be added to the wound dressing 110 including, but not limited to, a non-adherent layer (not shown) placed against the wound, one or more absorbent or wicking layers 160 between the wound and forward osmosis filter, one or more absorbent or wicking layers between the forward osmosis filter and the second layer (not shown), an oxygen permeable layer to allow oxygen transport to the wound (not shown), and/or a wound filling layer (not shown), for example. For NPWT, a vacuum distribution layer (not shown) may be employed. The vacuum distribution layer may include a more open structure, for example, an open cell foam. Even in non-NPWT wound dressings, this type of open layer may enhance distribution of oxygen to the wound to promote wound healing. One or more of the layers may be multi-functional. Multiple layers can be used for any of the additional layers. The absorbent layers are liquid holding layers and may be hydrophilic or hydrophobic material.

In FIG. 1A, wound dressing 110' comprises section 110A and section 110B. Section 110B is secured to the patient such as with a porous, tacky silicone wound contact and skin adherence layer 162. Section 110B includes forward osmosis filter 120. Section 110A is a removable/replaceable portion of wound dressing 110' in which Chamber 134' is formed between second layer 116 and third layer 125. Removing and changing out section 110A from wound dressing 110' provides for new osmotic agent 140 and new space for filtrate in new chamber 134'. Third layer 125 secures the osmotic materials 140 in place prior to use and allows the osmotic agent to contact the filter 120 during use. The third layer can be, for example, absorbent material that, along with the osmotic agent fills compartment 134'. A portion of the draw material can be imbedded in the absorbent material. The two sections of wound dressing 110', section 110A and section 110B, can be secured together, for example, by using tacky silicone layer 162 along the periphery. As another example, Section 110A can include a gel containing glycerin that acts as both an osmotic agent and water absorbing material. The gel can directly attach to the forward osmosis filter 120. The gel may be a gel pad and have a structure and shape that is formed and fabricated as a part of the manufacturing process, and the gel pad may remain as a gel pad throughout use, unlike powders (such as sodium polyacrylate or the like) or other materials that might be used to create a gel by absorbing water during or after patient use. Other materials can be integrated onto the surface of the gel pad or within the gel pad to enhance properties such as, but not limited to, liquid absorption, dispersion, evaporation, etc. The gel pad can have a hole or holes through it to allow water on the surface of the membrane to go through the hole(s) as liquid or water vapor.

FIG. 1B shows assembly 110C, which is an alternative construction to assembly 110B. This construction has an area or areas on the patient side of the forward osmosis membrane, such as portions of absorbent material 160 and wicking layer 161 exposed to cover layer 118 made at least partially of gas permeable material, such as polyurethane film with high MVTR, that allows for the transfer of water vapor out of this area through the high MVTR portions of the material. Through holes 166 or other open areas or cut-outs in the wicking layer 161 allow for greater fluid connection between the cover layer 118 and the area below wicking layer 161 including absorbent material 160. The cover layer 118 may also allow for the transfer of oxygen into the wound area to enhance the environment for would healing. The cover layer 118 provides a barrier to liquids, bacteria, and viruses to protect the wound. This configuration allows water to be removed from the wound exudate via a combination of water vapor transmission through the high MVTR material of the cover layer 118 and liquid water transmission through the forward osmosis membrane 120 using one or more preselected draw materials such as, but not limited to, glycerin, salts, or sugars.

The wicking layer 161 on the patient side of the forward osmosis membrane 120 distributes liquid across the membrane 120 and has been demonstrated to improve the transfer of water to the non-patient side of the membrane 120. Unintended air gaps between layers can reduce the ability of the exudate or water portion of the exudate to be accessible to the forward osmosis filter 120. To enhance effectiveness, some of or all of these layers can be partially or fully secured together with adhesive, heat, sonic welding, radio-frequency welding, ties, or other approaches. For example, FIG. 1B shows a slug of glue 168 securing the absorbent layer 160, the wicking layer 161, and the forward osmosis membrane 120 while the water vapor permeable film of the cover layer 118 is adhesive backed to secure the cover layer 118 to the other layers. The wound contact layer 162 is a silicone adhesive layer. For greater security, the cover layer 118 can be welded or otherwise bonded to the forward osmosis membrane 120.

In FIG. 1C, an embodiment for the glycerin gel pad assembly 148 containing the gel pad 146 and glycerin 141 is shown. On the X side of the gel pad 146 that connects to the forward osmosis membrane 120 is a material, such as but not limited to a first cellulose paper sheet 182 similar to a paper towel, that acts to distribute the glycerin 141 as well as water from the wound exudate across the surface of the first cellulose paper sheet 182 and therefore across the mating surfaces of the gel pad 146 and the forward osmosis membrane 120 either directly or through other layers. This configuration aids in keeping a large area of the forward osmosis filter 120 and a large area of the glycerin gel pad 148 active. The first cellulose paper sheet 182 may have a hole or holes 151 through it, or other open areas or cut-outs, allowing for some direct contact between the glycerin gel pad 148 and the forward osmosis membrane. The glycerin gel pad 148 may go through or partially through the hole or holes 151. On the other side, the Y side of the gel pad 146 is a material, such as but not limited to a second cellulose paper sheet 184 that acts to enhance evaporation of water. The surface of the second cellulose paper sheet 184 can have various configurations, such as dimples, pleats, raised rings, etc., that provide for greater surface area to further enhance evaporation. The second cellulose paper sheet 184 may also have a hole or holes 151 through it. The Y side surface of the gel pad 146 may also have various configurations, some of which may be similar to match those of the second cellulose paper sheet 184 and some which may be different, for example, to provide space for air to contact both sides of the second cellulose paper sheet 184. The first cellulose paper sheet 182 and second cellulose paper sheet 184 are connected together either directly or via an intermediate material or materials. Water mixed with glycerin wicks from the first cellulose paper sheet 182 to the second cellulose paper sheet 184 and spreads across the second cellulose paper sheet 184. Some of the water may be absorbed into the gel pad 146 and some of the water may evaporate off while some of the glycerin 141 may also be absorbed into the gel. Additional layers of material may be added to increase the water holding or water evaporating capabilities of the device. For example, an absorbent material that is non-laterally wicking or minimally laterally wicking may be used to keep absorbed water in a specific location away from the patient. While the connection between the first cellulose paper sheet 182 and the second cellulose paper sheet 184 is shown going around the gel pad, it may be beneficial to go through a hole in the gel pad 146. The first cellulose paper sheet 182 and second cellulose paper sheet 184 may be a unitary piece. The first cellulose paper sheet 182 and second cellulose paper sheet 184 may partially of fully enclose the gel pad 146 to form permeate/draw management assembly 143. Draw material, either glycerin or other, can be included in or on the first cellulose paper sheet 182 to enhance the initial efficiency of the forward osmosis process. A malleable gel that can be reshaped or a spreadable gel containing glycerin may be used as alternatives to the gel pad.

The gel pad assembly 148 of FIG. 1C may be used over the entire life of the dressing, such as 7 days under a physician's care, or can be replaced as needed depending on the amount of exudate and ability to evaporate off the filtrate water. The ability to replace the gel pad assembly 148 as needed allows for gel pads of different water absorbing volumes to be matched to the situation. For example, for a wound exuding up to 0.5 mL per hour, a gel pad assembly 148 capable of absorbing 12 mL could be used for one day and then replaced without any of the water evaporating off. The ability to replace the gel pad assembly 148 as needed also may be useful in situations where little evaporation is expected such as in a very humid environment. In another example, if the same gel pad assembly 148 could readily shed 6 mL of water in a day through evaporation, the gel pad assembly 148 could last 2 days. If the gel pad assembly 148 had capacity to absorb and hold 14 mL and daily shed 10 mL through evaporation, the gel pad assembly 148 could last the entire 7 days. If the wound exuded at a lower rate, a gel pad 146 with proportionately lower absorbing volume and evaporation volume capability could last the same number of days.

The gel pad 146 may be connected to a stiffer material to provide support and aid in maintaining its shape. The stiffer material may also aid in mating the gel pad 146 to the forward osmosis filter 120. The stiffer material can be internal or external to the gel, or a combination of both. The stiffer material can also provide for an area or areas to hold the gel pad 146 without contacting the gel or the glycerin.

FIG. 1C additionally shows a highly open material 156, such as but not limited to a menstrual pad top sheet or a film with small through holes or a plastic mesh, that when folded over and secured with releasable adhesive 154 forms a pocket 157 to secure the gel pad assembly 148 in place that readily allows for evaporation while keeping any water leakage to a minimum. A physical spacer 158, such as but not limited to a plastic woven mesh material, between the highly open material 156 and the paper sheet 184, can be used to further reduce the chance of liquid water leaking through the highly open material 156. The highly open material 156 as well as other components may include agents to prevent mold or bacterial contamination and growth. The gel pad assembly 148 can be otherwise secured in place using its natural tackiness, tape, adhesives, and other means.

Figure 1D:
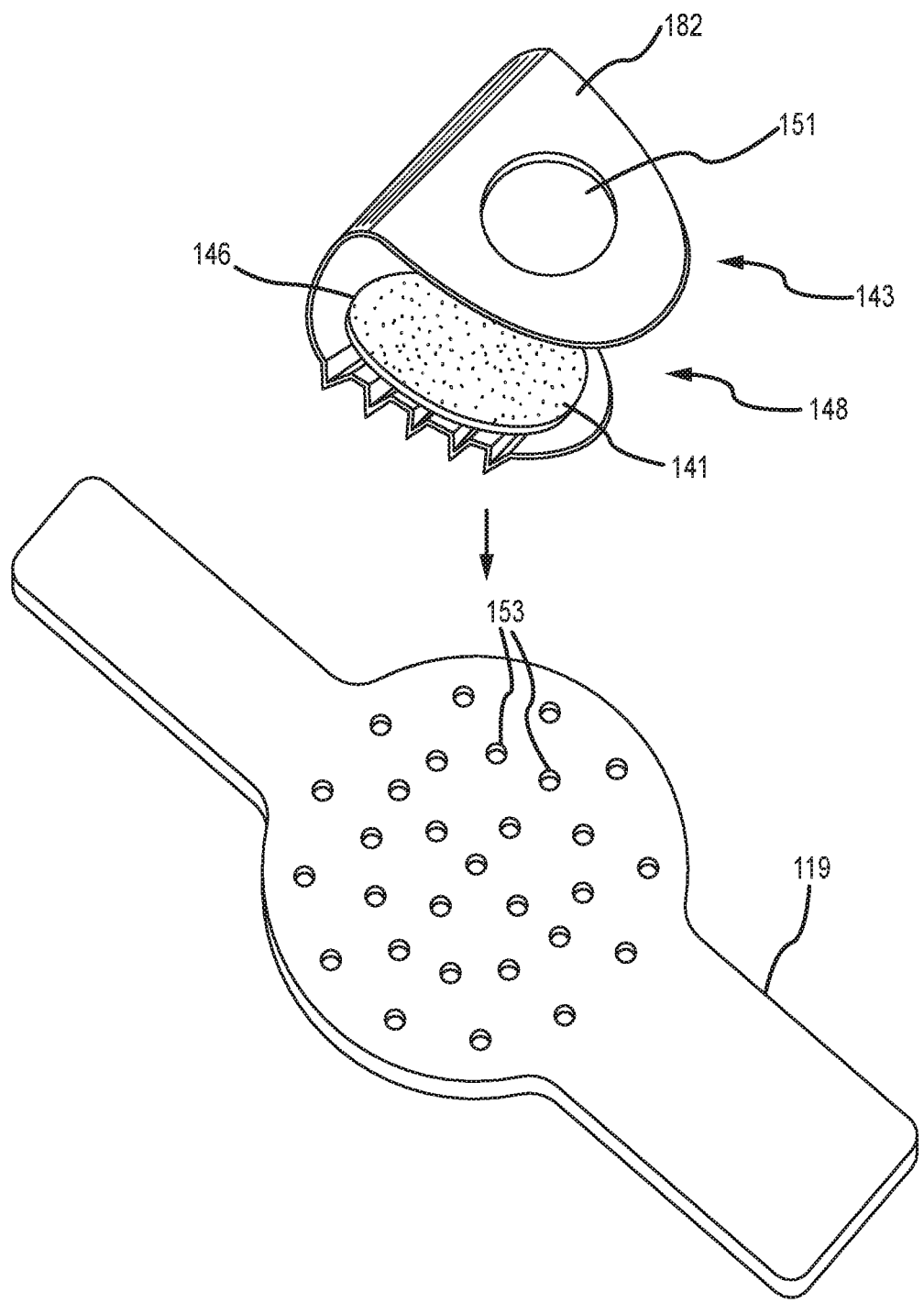
FIG. 1D is an exploded view of a gel pad and a plastic adhesive strip, according to an embodiment.

In FIG. 1D, the gel pad 146 or gel pad 146 with other components can be incorporated onto a plastic adhesive strip 119, similar to standard bandages sold under the Curad or Band-Aid brand names, and readily secured to interface with the forward osmosis membrane 120. The plastic adhesive strip 119 can have through holes 153 or be made of high MVTR film similar to cover layer 118 or both. While FIGS. 1C and 1D show a gel pad assembly 148, other materials that can hold the draw and make it available to the forward osmosis membrane 120 can alternatively be used.

Figure 1E:
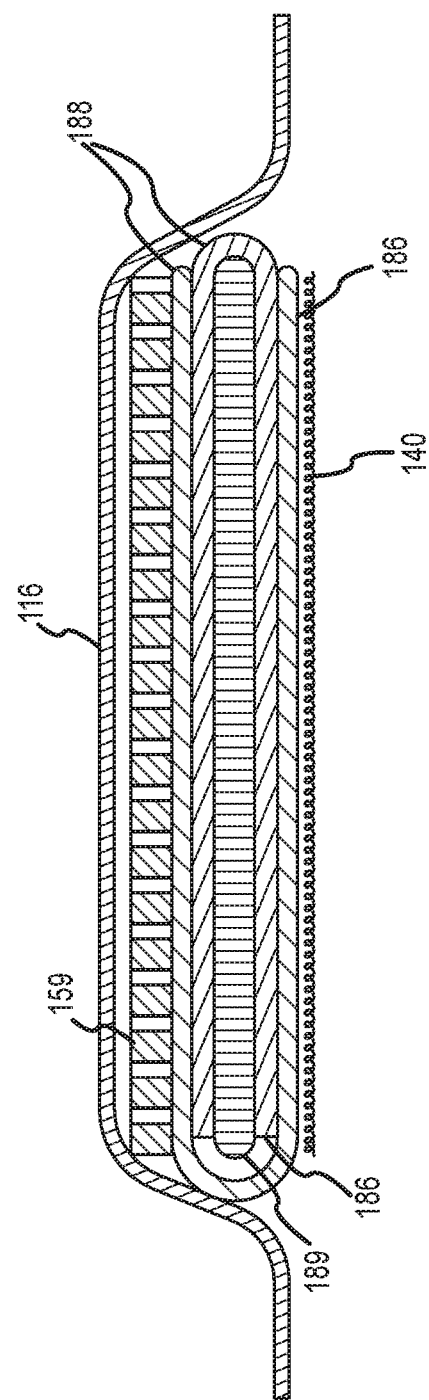
FIG. 1E is a cross-sectional view of section 110A of FIG. 1A, according to an embodiment.

FIG. 1E shows an alternative construction example of section 110A of FIG. 1A that includes a first set of one or more layers 186 of material with good absorption characteristics and good wicking characteristics impregnated with glycerin and/or other draw material 140 that is to be connected to the forward osmosis membrane 120. One or more of the first set of one or more layers 186 connects to a second set of one or more layers 188 whereby the connection allows water mixed with draw material 140 to move to the second set of one or more layers 188. The second set of one or more layers 188 can sequester the liquid by itself or with a secondary absorbent, such as with sodium polyacrylate, or encourage evaporation of the liquid, or a combination. The specific construction of the first set of one or more layers 186, the second set of one or more layers 188, the osmotic agent, the secondary absorbent, and/or the separating material depends on whether these materials on the non-wound side of the filter are to be refillable, replaceable, or last the life of the wound care dressing. This construction may also include a separating material 189 between the first set of one or more layers 186 and the second set of one or more layers 188 to force the liquid to wick around the separating material and is intended to reduce the movement of draw material 140 directly through the first set of one or more layers 186 to the second set of one or more layers 188. As more draw material 140 moves to the second set of one or more layers 188 over time, the layers can be manually switched so the second set of one or more layers 188 becomes positioned at the forward osmosis membrane 120 and the first set of one or more layers 186 collects the water mixed with draw material. The second set of one or more layers 188 may also initially contain draw material 140. Without the separating material 189 or without otherwise separating the first set of one or more layers 186 and the second set of one or more layers 188, the draw material 140 concentrates with evaporation of the water and can be self-recycling as the draw material feeds back to the first set of one or more layers 186, allowing for continued use without replacing or replenishing the draw material 140. The second set of one or more layers 188 can be extensions of the first set of one or more layers 186 and can be positioned in different directions, for example on top of or to the side of the first set of one or more layers 186. Extra draw material 140 can also be accessible from various locations in the dressing, including but not limited to extensions off one or more of the first set of one or more layers 186, preferably the layer closest to the forward osmosis membrane 120. If the second layer 116 has one or more openings in the material, a porous spacer 159 between the absorbent material and the second layer 116 reduces the potential for liquid water mixed with draw materials 140 or for raw draw materials from leaking out.

In FIG. 2, the wound dressing 210 with forward osmosis filter 220 has at least one access port 242 on second layer 216 for input or removal of material into the chamber or chambers 234. For example, brine can be added into a chamber or chambers 234 through the access port(s) 242. As another example, wound exudate fluid that has gone through the forward osmosis filter 220 into the chamber or chambers 234 and mixed with the draw material can be removed via the port(s) 242. The access port 242 can be a syringe port which is normally closed and where the syringe needs to be engaged to open the valve in the access port 242. Other types of ports or access openings can be used. Additionally, the access port 242 can be used for access of a sensor to monitor the fluid in the chamber.

Measurement examples include, but are not limited to, fullness of the chamber and salinity. The chamber can be emptied via a vacuum pump, such as a peristaltic pump, attached to the chamber(s) 234. Emptying can be done automatically.

FIG. 3 shows a forward osmosis filter wound dressing 310 connected to a secondary compartment 390 for collection or management of fluids. The transfer of fluid across the forward osmosis filter creates pressure in chamber 334 and can drive the fluid out of chamber 334 to the secondary collection compartment 390. The system can also be primed by having the draw materials (not shown) extend from the chamber(s) 334 to the secondary compartment 390. Draw materials in the secondary collection compartment 390 can be transferred to the chamber 334. The secondary collection compartment 390 allows for a greater volume of fluid to be collected without necessarily being directly at the wound site. The secondary collection compartment 390 can be optionally removable and replaced, for example if full or uncomfortably heavy for the patient.

A valve as shown in FIG. 2 can be used to open or close access to a second chamber 316 of the wound dressing 310. A valve can also be used to open or close access to the secondary collection compartment 390. The secondary collection compartment 390 can also be made or partially made of materials with a high moisture vapor transmission rate that allows for the fluid volume collected in the compartment to be reduced. Fluid can also be removed from the dressing 310 or the secondary collection compartment 390 via a vacuum pump, peristaltic pump, gravity, or other fluid driver.

The secondary collection compartment 390 can contain one or more absorbent layers or wicking layers (not shown). This secondary collection compartment 390 can be connected to the wound dressing chamber by an extended passageway, such as tubing, allowing for positioning the secondary collection compartment 390 in a location separate from the wound, for example, attached to the patient's belt. Connection 368 allows for opening, removal, or replacement of either wound dressing 310 or secondary collection compartment 390. The secondary collection compartment 390 may also be useful in wound drainage systems that do not use a forward osmosis filter.

Figure 4:
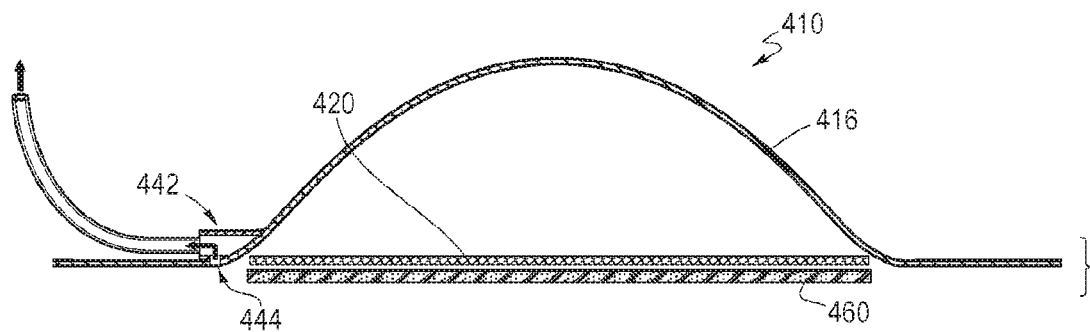
FIG. 4 is a partial cross-sectional drawing of a forward osmosis wound dressing with connected NPWT device, according to an embodiment.

FIG. 4 shows a forward osmosis filter wound dressing 410 in conjunction with a NPWT pump (not shown). The configuration of the wound dressing and location of the pump attachment are constructed to minimize the potential of any exudate from being sucked into the pump tubing or the pump. For example, access opening 444 can be covered with a filter material (not shown) that allows air but not exudate and retentate to pass through it. Other approaches such as creating a long passageway filled with open structure material such as gauze or foam extending from the active portion of the wound dressing to the NPWT adapter 442 and access opening 444 can prevent or inhibit exudate from going to the pump while still providing a path for application of the vacuum from the NPWT pump.

A vacuum from the NPWT pump is applied only to the wound side of the forward osmosis membrane or filter 420. At the same time, water in the exudate is pulled through the forward osmosis filter 420 by osmotic agents (not shown) and is captured between the forward osmosis filter 420 and the second layer 416. This captured water on the non-wound side of the forward osmosis membrane or filter 420 is separate from and not connected to the NPWT vacuum. Other layers and materials can be incorporated as previously described. Foam or gauze 460 are commonly used in filling the wound in traditional NPWT.

Alternatively, forward osmosis can work in combination with a canister collection system where some exudate can be sucked into the pump tubing. This provides a dual action for managing exudate. An optional third path for managing the exudate is through the use of a material fluidly connected to the wound area that has high water vapor transmission properties to allow for evaporation of a portion of the water content of the exudate. This may allow for a small size canister or other collection device, for example a small bag with foam sealed inside, to be used and may extend the life of the wound dressing.

Figure 5:
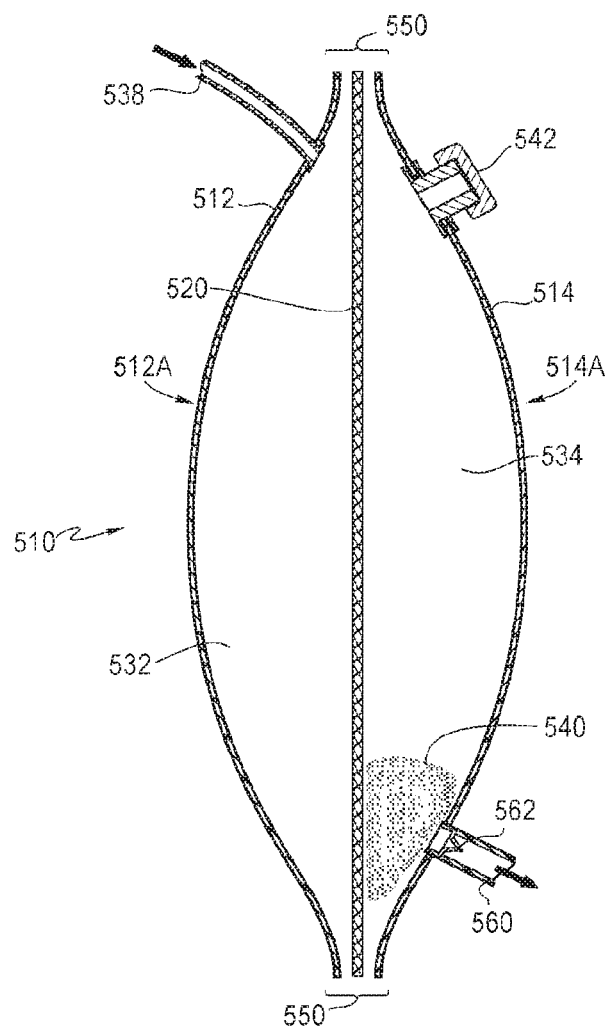
FIG. 5 is a partial cross-sectional drawing of a biological waste fluid collection bag with internal forward osmosis filter, according to an embodiment.

FIG. 5 shows a fluid collection bag 510 with a filter material 520 capable of allowing water to pass through the filter via osmotic pressure while preventing or inhibiting most of the bacteria and viruses from passing through. In this embodiment, the filter is sealed at the perimeter 550 between the two sheets 512 and 514 of the collection bag 510, thereby creating two separated compartments or chambers 532 and 534. The inlet 538 to the first compartment 532 is located on the first sheet side 512A of the bag and allows the biological waste fluid to enter between the first sheet 512 of the collection bag 510 and the filter 520, preferably directly from the patient. The inlet allows for single, periodic, or continual input of fluid into the first chamber 532.

The outlet 560 from the second compartment 534 is located on the second sheet side 514A of the bag 510 and allows the water that passes through the filter 520 from the first chamber 532 to the second chamber 534 to be emptied from the collection bag 510. The outlet 560 can allow for single, periodic, or continual emptying of the second chamber 534. The outlet 60 in this embodiment has a mechanical valve 562 that preferably allows for one-way flow out of the bag 510. Other mechanical or electromechanical approaches for opening the outlet 560 can be used and can even include automated activation of the valve 562 based on a set volume.

The second chamber includes the draw solute(s) 40 which can be added during or post-manufacture of the device. A separate opening 542 can be included on the second sheet side 514A of the bag 510 to provide access for adding draw material(s) 540. Other items can be added into the chambers of the bag such as for reducing odor, reducing bacterial or viral load, blocking or binding or transforming specific components present in the biological waste fluid, or absorbing left over liquid or the like.

In alternative embodiments (not shown), the container can be a rigid container or a combination of rigid and flexible materials. The container can have multiple inputs. The outlet port can attach to tubing to allow transfer of the water, and other materials in the water, to a selected location for disposal such as a sink or toilet.

As filtrate volume is increased in the second compartment, especially if the compartment is rigid or otherwise constrained, pressure created by the increase in filtrate volume within the compartment can be harnessed to open the outlet valve to expel a portion of the filtrate. In another embodiment (not shown) the inlet port is connected to tubing with a suction canister port connection on it to allow transfer of collected fluid from the canister. The tubing can be put into a peristaltic pump to drive the collected fluid from the suction canister port into the fluid collection bag.

In yet another embodiment (not shown), no outlet is provided or an outlet is created post-manufacture, for example by piercing the container with a spiked connector.

In yet another embodiment (not shown) a forward osmosis device is used for larger volumes or even bulk collections of biological waste fluids, potentially from different sources. It is of larger scale than the forward osmosis device described.

Figure 6:
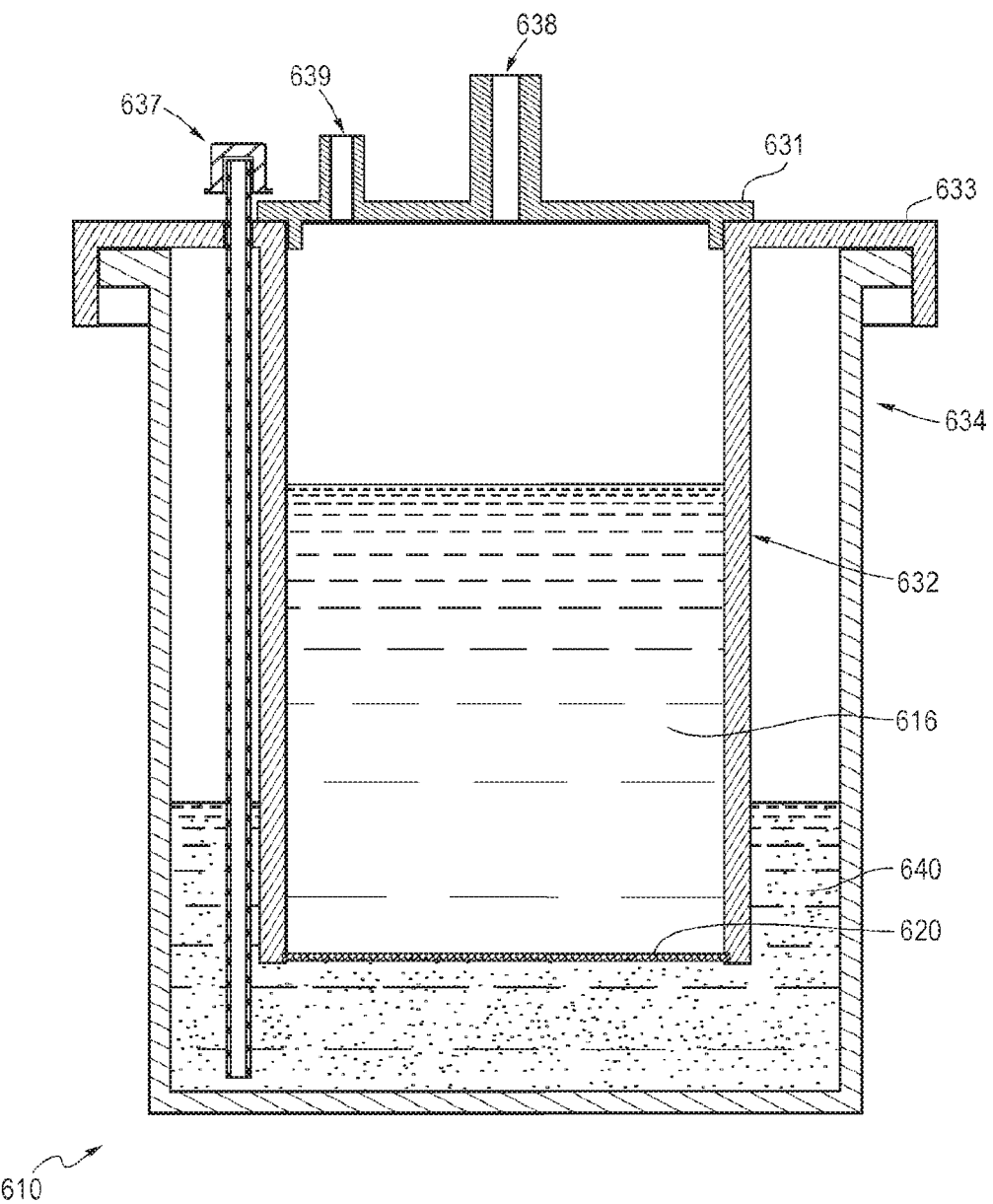
FIG. 6 is a cross-sectional drawing of a suction canister with integrated forward osmosis filter, according to an embodiment.

In FIG. 6, the forward osmosis filter 620 is incorporated into a canister, such as a suction canister 610. Biological waste fluid 616 enters the receiving chamber 632 of canister 610 through the inlet port 638 via a vacuum pump connected to vacuum port 639. Alternatively, a peristaltic pump, gravity, or other fluid driver can be used. The forward osmosis filter 620 is secured to the receiving chamber 632. The receiving chamber 632 is inside a second chamber 634 which holds the draw solute(s) 640 and the resulting filtrate. The second chamber 634 never contacts the original biological waste fluid 616 or any resulting retentate from the filtration process. Access port 637 allows for osmotic agent to be added the second chamber 634 and also allows for removal of fluid, which is a combination of filtrate and draw solute(s). Addition or removal of fluids to or from either chamber may be accompanied by air replacement such as by incorporating a filtered air vent (not shown) in the lid(s) 631 and 633. Lid 633 covering a portion of second chamber 634 can be integrated into receiving chamber 632.

A portion of water in the filtrate can be vaporized by adding heat or by other methods to keep the draw solution concentrated. Advantageously, this can reduce the amount of draw material required and associated need for refilling of draw material while reducing the amount of fluid that is otherwise stored and possibly emptied from the second chamber 634.

Figure 7:
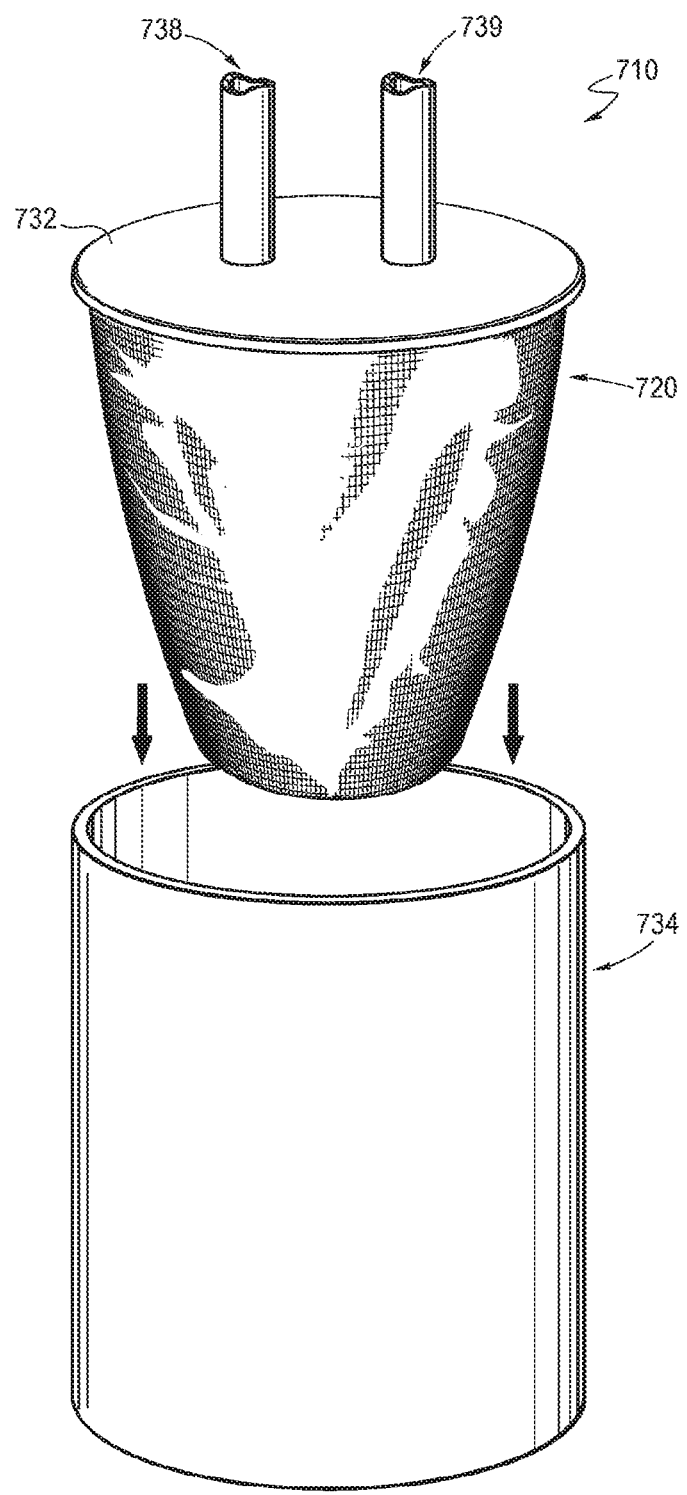
FIG. 7 is a perspective view of a forward osmosis filter bag as part of a suction canister, according to an embodiment.

FIG. 7 shows a forward osmosis filter bag 710 made from filter material 720 as an alternative configuration of the receiving chamber 632 from FIG. 6. A rigid support (not shown) may be included inside the filter bag if needed to hold the bag open, especially if fluid is being delivered into the bag via suction. Biological waste fluid can be drawn into the system by attaching a vacuum source to vacuum port 739 on lid 732. The biological liquid or semi-liquid waste enters the forward osmosis filter bag 710 via port 738 on lid 732. Draw materials and associated filtrate are in second chamber 734.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and exemplary embodiments have been disclosed herein, other aspects and embodiments will be apparent to those skilled in the art. The various aspects and exemplary embodiments disclosed herein are for the purposes of illustration and are not intended to be limiting.

I claim:

1. A wound treatment device comprising:
   a filter incorporated into a wound dressing and configured to be placed over a wound area and secured to a patient, the filter having a wound side and a non-wound side opposite to the wound side and including a semi-permeable forward osmosis filter or a semi-permeable forward osmosis membrane configured to:
   remove liquid water from wound drainage fluid by allowing the liquid water to pass through the filter and inhibiting other components in the wound drainage fluid from passing through the filter such that the liquid water is substantially free of the other components,
   prevent substantially all liquids and bacterial contaminants from passing through the filter in the reverse direction toward the wound area;
   wherein the filter includes glycerin as an osmotic agent or glycerin as a draw material at a first location effective to provide at least some of the osmotic potential to passively transport at least a portion of the liquid water from the wound drainage fluid through the filter without application of electrical energy or electrochemical energy;
   a cover layer directly or indirectly connected to the filter to form a protective barrier over the wound and prevent ingress of liquids, bacteria, and viruses to the wound area, the cover layer including at least a portion of semi-permeable high moisture vapor transmission rate material that is fluidly connected with the wound drainage fluid in the wound area such that at least some of the water from the wound drainage fluid passes through the high moisture vapor transmission rate material as water vapor, thereby aiding in overall water removal from the wound area to complement the liquid water removed through the filter; and
   one or more absorbent materials positioned on the non-wound side of the filter opposite to the wound side of the filter and in fluid communication with the filter such that the filter is between the one or more absorbent materials and the wound area effective for the one or more absorbent materials to absorb at least a portion of the liquid water mixed with the draw material.

2. The wound treatment device of claim 1, wherein at least one of the one or more absorbent materials is removable and replaceable.

3. The wound treatment device of claim 1, further comprising a supportive backing material positioned on a non-wound, non-patient side of the filter, wherein the filter includes glycerin, the supportive backing material containing more glycerin than the glycerin on a wound side of the filter.

4. The wound treatment device of claim 1, further comprising at least one of a high moisture vapor transmission rate material or a material having areas open to the surrounding air positioned on a non-wound side of the filter, wherein at least one of the high moisture vapor transmission rate material or the material having areas open to the surrounding air facilitate evaporation of at least some of the liquid water after the liquid water has been moved to the non-wound side of the filter.

5. The wound treatment device of claim 1, further comprising one or more other locations of osmotic agent or draw material positioned on a non-wound side of the filter to be in contact with the filter for at least some portion of a time the wound dressing is applied to the patient, the one or more other locations of osmotic agent or draw material different from the first location of the osmotic agent or draw material of the filter.

6. The wound treatment device of claim 1, further comprising at least one chamber or compartment, the at least one chamber or compartment configured to collect liquid or permeate processed by the wound treatment device and securable to the forward osmosis membrane.

7. The wound treatment device of claim 6, further comprising at least one of an absorbent layer or a wicking layer in the at least one chamber or compartment.

8. The wound treatment device of claim 7, wherein the absorbent layer or wicking layer is removable or replaceable from the at least one chamber or compartment.

9. The wound treatment device of claim 6, wherein the at least one chamber or compartment is removable and replaceable from the filter.

10. The wound treatment device of claim 6, wherein the filter or an area around the filter is secured to a second layer of material to form the at least one chamber or compartment, the second layer of material configured to provide a water vapor transmission rate of at least about 1000 $g/m^2/24$ hours.

11. The wound treatment device of claim 6, further comprising a port providing access to the at least one chamber or compartment, the port being sized and dimensioned for addition or removal of materials from the at least one chamber or compartment that includes the non-wound side of the filter.

12. The wound treatment device of claim 1, wherein the wound treatment device is part of a negative pressure wound therapy system.

13. The wound treatment device of claim 1, wherein the material includes a wicking layer positioned on the wound treatment device to be between the wound and the filter, the wicking layer configured to distribute liquid from the wound exudate over a larger area of both sides of the wicking layer and thus direct contact with a larger area of the filter thereby enhancing the transfer of the liquid water to a non-wound side of the filter.

14. A system for treating and healing wounds, the system comprising:
a forward osmosis wound dressing device having a forward osmosis filter and a confined space on a non-wound side of the filter, the confined space containing glycerin as an osmotic agent, the wound dressing configured to cover a wound and transport at least some portion of a water component of a wound fluid exudate away from the wound through the forward osmosis filter and then into the confined space on the non-wound side of the filter, the confined space containing one or more absorbent materials to absorb at least one of the glycerin, the water component, or a mixture of the glycerin and the water component, the confined space limiting an amount of filtrate mixed with draw material contained in the confined space;
a port fluidly connected to the confined space, wherein when the confined space is full or nearly full of liquid, water coming through the filter forces the filtrate mixed with the draw material out of the confined space via the port and out of the wound dressing device;
a secondary collection compartment fluidly connected or connectable to the wound dressing device through the port and configured to collect the filtrate transported out of the wound dressing device; and
additional draw material connected or connectable to the confined space.

15. A system for negative pressure wound therapy dressing for a wound area, the system comprising:
a vacuum access port for application of a vacuum to the wound area; and
a forward osmosis membrane or filter configured to remove water from at least some portion of wound exudate of the wound area, the forward osmosis membrane or filter including:
a draw material including glycerin at a first location and configured to passively transport at least a portion of liquid water from wound drainage fluid of the wound area through the forward osmosis membrane or filter;
a supportive backing material positioned on a non-wound side of the dressing, the backing material containing more glycerin than the glycerin on a wound side of the forward osmosis filter;
one or more other locations of additional draw material on the non-wound side of the forward osmosis membrane or filter, the additional draw material from at least one of the one or more other locations positioned to be in contact with the forward osmosis membrane or filter for at least some portion of time the dressing is applied to the patient, the one or more other locations of additional draw material being different from the first location of the draw material; and
a cover layer directly or indirectly connected to the forward osmosis membrane or filter to form a protective barrier over the wound area effective to prevent ingress of liquids, bacteria, and viruses to the wound area, the cover layer including at least a portion of semi-permeable high moisture vapor transmission rate material that configured to be fluidly connected with the wound exudate in the wound area to allow at least some of the water from the wound exudate to pass through the high moisture vapor transmission rate material as water vapor, thereby aiding in overall water removal from the wound area to complement the water removed through the forward osmosis filter, the high moisture vapor transmission rate material being configured to provide a water vapor transmission rate of at least about 1000 $g/m^2/24$ hours.

16. The system of claim 15, wherein some portion of the water exudate is removed and transported away from the dressing via the vacuum for collection into a container.

17. The system of claim 15, further comprising a second collection compartment for managing wound exudate fluid, wherein the secondary collection compartment is:
configured to have a connection point connectable to a wound dressing;
separated from the wound dressing;
configured to store liquid entering the secondary collection compartment via the connection point; and
located near the patient.

18. A wound dressing, comprising:
a forward osmosis filter having a wound side of the filter and a non-wound side of the filter, wherein the filter contains glycerin on at least the non-wound side of the filter, provides a protective barrier for a wound whereby bacteria and viruses do not pass through the filter from the non-wound side of the filter, includes an area on the wound side of the forward osmosis filter for containing wound exudate having a water component; and
one or more absorbent materials containing glycerin, the one or more absorbent materials directly or indirectly mating with the non-wound side of the filter; and
a cover layer directly or indirectly connected to the filter, the cover layer including at least a portion of semi-permeable high moisture vapor transmission rate material such that at least some of the water component passes through the high moisture vapor transmission rate material as water vapor;
wherein the filter is capable of retaining non-water components from the wound exudate on the wound side of the filter; and
wherein the absorbent material is capable of absorbing at least a portion of said water component from the wound exudate that passes through the filter from the wound side to the non-wound side of the filter.

19. The wound dressing of claim 18, wherein the absorbent material containing glycerin is a gel containing glycerin.

* * * * *